(12) United States Patent
Terragno et al.

(10) Patent No.: US 9,474,300 B2
(45) Date of Patent: Oct. 25, 2016

(54) FERMENTED FOOD PRODUCTS CONTAINING PROBIOTIC STRAINS

(75) Inventors: Luc Terragno, Meudon (FR); Francois Debru, Versailles (FR); Phillippe Tessier, Palaiseau (FR); Stephane Herve, Madrid (ES); Jean-Michel Faurie, Jouy-en-Josas (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 0 days.

(21) Appl. No.: 13/416,381

(22) Filed: Mar. 9, 2012

(65) Prior Publication Data

US 2012/0171162 A1    Jul. 5, 2012

Related U.S. Application Data

(60) Division of application No. 12/013,685, filed on Jan. 14, 2008, now Pat. No. 8,158,172, which is a continuation of application No. PCT/FR2006/001688, filed on Jul. 11, 2006.

(30) Foreign Application Priority Data

Jul. 13, 2005   (FR) .................................... 05 07529

(51) Int. Cl.
| | | |
|---|---|---|
| *A23C 9/12* | (2006.01) | |
| *A23L 1/30* | (2006.01) | |
| *A23C 9/123* | (2006.01) | |
| *A23C 9/13* | (2006.01) | |
| *A23C 11/10* | (2006.01) | |

(52) U.S. Cl.
CPC ............ *A23L 1/3014* (2013.01); *A23C 9/1234* (2013.01); *A23C 9/1322* (2013.01); *A23C 11/106* (2013.01)

(58) Field of Classification Search
CPC   A23C 9/1234; A23C 9/1322; A23C 11/106; A23L 1/3014
USPC ...................... 426/34, 42, 43, 580, 582, 583
See application file for complete search history.

(56) References Cited

U.S. PATENT DOCUMENTS 5,895,648  A    4/1999  Cavaliere Vesely et al.

FOREIGN PATENT DOCUMENTS

| EP | 0 281 476 A | 9/1988 |
|---|---|---|
| FR | 2 842 707 A | 1/2004 |
| RU | 2 169 763 C1 | 6/2001 |

OTHER PUBLICATIONS

Dave R I et al., "Ingredient Supplementation Effects on Viability of Probiotic Bacteria in Yoghurt", Nov. 1998, pp. 2804-2816.
Dechter T H et al., "Survivability and Beta-Galactosidase Activity of Bifidobacteria Stored At Low Temperatures", 1998, pp. 73-89.

*Primary Examiner* — Leslie Wong
(74) *Attorney, Agent, or Firm* — Arent Fox LLP

(57) ABSTRACT

The use of at least one sulphur-containing amino acid, at a total concentration of about 5 to 75 mg/ml, in particular of about 5 to about 50 mg/l, in particular of about 5 to about 30 mg/l, in particular of about 5 to about 20 mg/l, in free form, for implementing a method for preparing a fermented food product fermented by ferments containing *bifidobacteria*, the food product has acceptable sensory properties, contains more than about $5 \times 10^7$, in particular more than about $10^8$ *bifidobacteria* per gram of food product fermented for a shelf lifetime of at least 30 days, in particular a shelf lifetime of at least 35 days, and containing no more than 0.5% of yeast extract or of yeast autolysate.

18 Claims, 4 Drawing Sheets

FERMENTED FOOD PRODUCTS CONTAINING PROBIOTIC STRAINS

CROSS-REFERENCE TO RELATED APPLICATIONS

Figure 1:
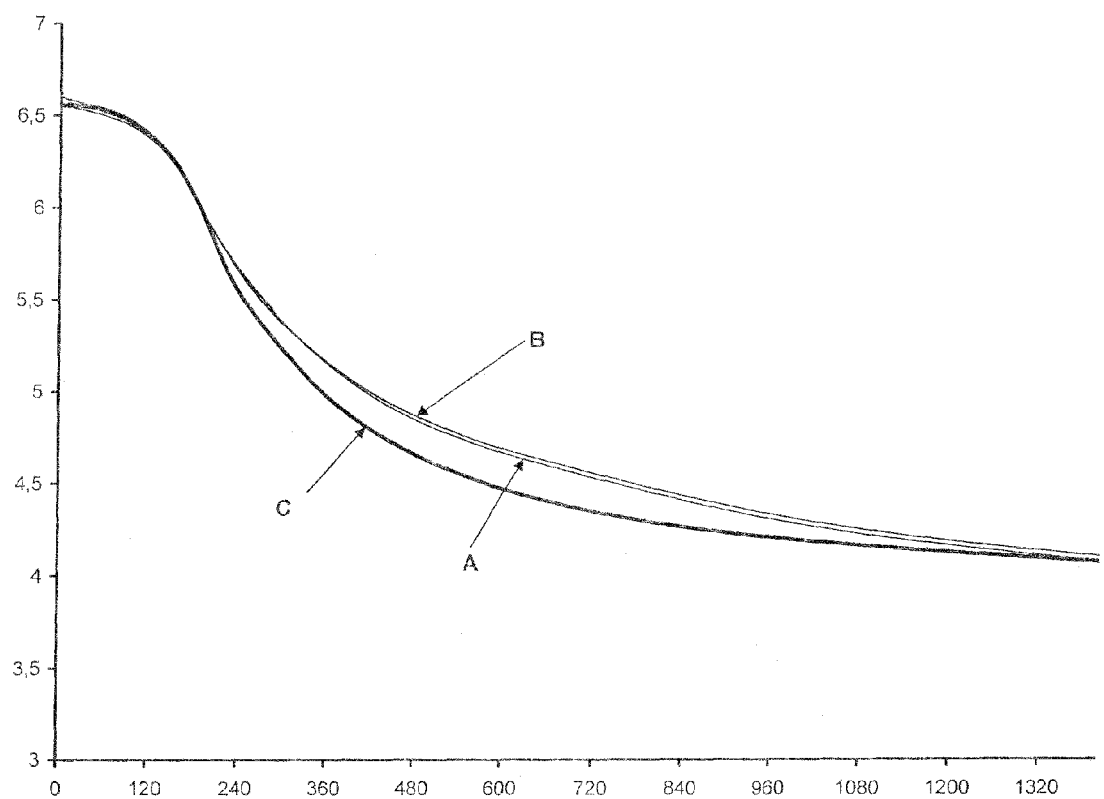

This application is a divisional of U.S. patent application No. 12/013,685 filed Jan. 14, 2008 which is a Continuation of PCT Application No. PCT/FR2006/001688 filed Jul. 11, 2006 which claims priority to French Application No. 0507529 filed Jul. 13, 2005.

BACKGROUND OF THE INVENTION

1. Field of the Invention

The invention relates to fermented food products containing probiotic strains, and their preparation process.

1. Description of the Related Art

The *bifidobacteria* belong to the dominant anaerobic flora in the colon. The main species present in the human colon are *Bifidobacterium adolescentis, Bifidobacterium bifidum, Bifidobacterium longum* ssp *infantis, Bifidobacterium breve, Bifidobacterium longum*.

The *bifidobacteria* are probiotic bacteria of choice. Bacteria of the genus *Bifidobacterium* are used in numerous products currently on the market and are often added to dairy products already comprising the standard bacteria in yogurt (*Streptococcus thermophilus* and *Lactobacillus bulgaricus*).

The consumption of *bifidobacteria* is recognized as being beneficial in the process of re-establishing the normal *bifidobacteria* population in individuals having undergone antibiotics therapy. This consumption also seems to make it possible to reduce constipation, prevent diarrhoea and reduce the symptoms of lactose intolerance.

Probiotics are live bacteria. The use of these live bacteria in the manufacture of food products such as dairy products is tricky in particular with regard to the problem of survival of these bacteria in the product.

80% of the products currently on the market which contain *bifidobacteria* do not satisfy the criteria making it possible to maintain that they significantly improve the intestinal transit of the individuals consuming them. A daily intake of at least $10^8$ to $10^9$ viable cells has been recommended as the minimum dose making it possible to have a therapeutic effect (Silva A. M., Barbosa F. H., Duarte R., Vieira L. Q., Arantes R. M., Nicoli J. R., Effect of *Bifidobacterium longum* ingestion on experimental salmonellosis in mice, 0.1. Appl. Microbiol. 97 (2004) 29-37). The required dose can be dependent on the probiotic strain used.

In the case of the production of a bioactive food product containing *bifidobacteria* the problem therefore arises of obtaining a sufficient population of these bacteria in the product and maintaining it during the "life" of the product without resorting to technical solutions capable of altering the organoleptic qualities of the product.

The problem of the numerical size of the population of probiotic strains in a fermented dairy product is a known problem (see in particular D. Roy, Technological aspects related to the use of *bifidobacteria* in dairy products, Lait 85 (2005) 39-56, INRA, EDP Sciences).

Several reasons for this problem have been suggested, including the reduction in the population during storage, the disturbed growth of these bacteria starting from a certain pH or quite simply the poor ability of these *bifidobacteria* to grow, in particular in milk.

It is known that the fructo-oligosaccharides, certain starches, certain sugars, glycerol and certain yeast extracts have significant bifidogenic effects. On the other hand oxygen is toxic to certain probiotic strains.

The use of cysteine or ascorbate as an oxygen scavenger has therefore been described (A review of oxygen toxicity in probiotic yogurts: influence on the survival of probiotic bacteria and protective techniques. Talwalkar & Kailasapathy; Comprehensive Reviews in Food Science and Food Safety, 3 (3) 117-124; 2004), without it however having been demonstrated that the use of these substances makes it possible to obtain and maintain populations of *bifidobacteria* at the desired levels during storage. Moreover, the potentially negative effect of the cysteine on the final properties of a yogurt has been noted.

Generally, the fermented food products having properties of relative maintenance of the populations of *bifidobacteria* during the preservation of said products, and which are described in the literature, do not generally have acceptable organoleptic properties, due to the fact in particular that substances such as yeast extract are present in a high concentration in the products.

SUMMARY OF THE INVENTION

The main purpose of the invention is to provide fermented food products having acceptable organoleptic properties and containing a high concentration of *bifidobacteria* at the end of the fermentation period and throughout the preservation period of said fermented food products.

The main purpose of the invention is to provide fermented food products containing *bifidobacteria* in a good physiological state and having a significant survival rate during the period of preservation of said fermented food products, in particular up to the use-by date of the products.

Another purpose of the invention is to provide preparation processes which are simple to implement, making it possible to obtain the above products.

Another purpose of the invention is to promote the growth of the *bifidobacteria* in relation to the standard symbioses present in yogurts, these symbioses being constituted in a standard fashion by one or more strains of *Streptococcus thermophilus* and of *Lactobacillus bulgaricus*.

The purposes of the invention are achieved thanks to the surprising finding made by the inventors that the incorporation of sulphur-containing amino acids in the starting substance during the preparation of fermented food products containing *bifidobacteria*, in a small enough quantity not to alter the organoleptic properties of the products, makes it possible to obtain rapidly, after fermentation of the populations, at least $5.10^°$ or even $10^8$ *bifidobacteria* per gram of product, and increased survival of the *bifidobacteria* up to the use-by date of the products, without necessarily modifying the growth of the other bacterial strains.

The invention relates to the use of at least one sulphur-containing amino acid, at a total concentration of approximately 5 to approximately 75 mg/l, in particular approximately 5 to approximately 50 mg/l, in particular approximately 5 to approximately 30 mg/l, in particular approximately 5 to approximately 20 mg/l in the free form, for the implementation of a process for the preparation of a fermented food product using ferments containing *bifidobacteria*, which fermented food product has acceptable organoleptic properties, contains more than approximately $5.10^7$, in particular more than approximately $10^8$ *bifidobacteria* per gram of fermented food product for a preservation period of at least 30 days, in particular at least 35 days and does not contain more than 0.5% of yeast extract or yeast autolysate.

By "sulphur-containing amino acid" is meant cysteine (L-cysteine) or methionine as well as their derivatives, optionally in the form of a salt.

In particular there can be used according to the invention monohydrated L-cysteine hydrochloride (monohydrated (R)-2-amino-mercaptopropionic acid monohydrochloride) or L-methionine ((S)-2-amino-4-methylthio-butyric acid), of the respective formulae:

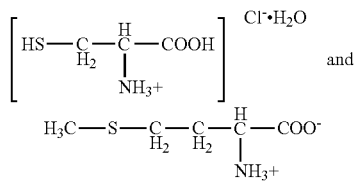

By "in the free form" is meant amino acids which are not bound to other amino acids by a peptide bond within peptides, polypeptides or proteins.

Preferably, the sulphur-containing amino acids according to the invention are used in reduced form, i.e. the sulphhydryl group —SH is reduced. This preferred form of the sulphur-containing amino acids therefore excludes in particular cystine, the oxidized form of cysteine involving the combination of two cysteines via a disulphide bridge.

The *bifidobacteria* being substantially without proteolytic activity, it is advantageous to use the abovementioned amino acids in the free form so that they can be directly assimilated by the *bifidobacteria*.

The sulphur-containing amino acid or acids used according to the invention are advantageously filtered beforehand and/or autoclaved (or pasteurized, i.e. treated at a temperature above 50° C.) and/or irradiated, in order to take account of the constraints of use as regards microbiological contamination, i.e. so that they are substantially without microbial contaminants.

If the sulphur-containing amino acids are used at a concentration above 75 mg/l, a degradation of the organoleptic properties of the food product is noted.

If the sulphur-containing amino acids are used at a concentration below 5 mg/l, the population of *bifidobacteria* greater than $5.10^7$ or $10^8$ CFU per gram of product cannot generally be maintained during the preservation period of the product.

It should be noted that the concentration of sulphur-containing amino acids used according to the invention relates to the sulphur-containing amino acid or acids especially added during the preparation of the products. This concentration does not take account of the possible bacterial production of sulphur-containing amino acids during the preparation nor even of the quantity of sulphur-containing amino acids in the free form which are naturally present in the starting substance which serves to prepare the food product (for example in milk) or in the adjuvants which can be used during the preparation.

The typical concentration of sulphur-containing amino acids present in milk is 100 to 1300 mg/l including approximately 260 mg/l cysteine and 1020 mg/l methionine (Handbook of Milk composition, 1995, Academic Press). It should be noted that the vast majority of these sulphur-containing amino acids present in milk is in the bound form in peptide or protein chains.

By "ferments" is meant a set of bacteria, in particular bacteria intended for fermentation and/or bacteria with probiotic value.

By "acceptable organoleptic properties" is meant in particular the absence of an undesirable sulphur-type taste, as determined by a standard sensory analysis test, which can correspond to the protocol described hereafter.

The sensory mechanism starts with the generation of a stimulus following the consumption of a product. This stimulus allows a perception which is dependent on genetic and physiological factors in the individual consumer. This perception is then verbalized (a list of words is proposed to the consumer) then quantified (use of ranges). The consumer then gives an overall assessment of the product that he has consumed (this assessment is influenced by his culture, his experiences) and says whether or not he would be prepared to buy this product (data such as cost, communication about this product can then be provided).

Sensory analysis is a science based on perception (physiological and psychological) involving the five senses (taste, smell, sight, hearing, touch) and using very rigorous protocols.

The consumers constituting the panel who carry out the sensory analyses are selected for their sensory abilities, their abilities in terms of verbalization, their abilities in terms of use of ranges for an assessment and their abilities to work in a group (in order to obtain a consensus). It is absolutely necessary to verify that the assessments of the panel members are repeatable, reproducible, with a homogeneity in terms of discrimination and in terms of classification. Tests making it possible to verify these pre-requisites are repeated several times. The choice of products is made according to three main criteria: according to the age of the product (products of the same age are chosen), these products must be representatives in the case of a standard assessment and the products are homogeneous (few differences between them). These products are presented anonymously and in coded form, in a certain order and homogeneously (same temperature etc.).

The environmental conditions of the sensory analysis are important: the conditioned air, the lighting, the sound environment, the decoration (neutral if possible) and the odour of the room in which the analysis is carried out should be standardized. The panel members are separated by cubicles. They should not smoke, consume coffee or menthol in the hours preceding the analysis session. They should also not wear perfume or make-up.

At the end of this analysis, a product is to be considered as having "acceptable organoleptic properties" if the panel members have not detected an undesired sulphur-type taste in this product.

The preservation or storage period of the fermented food product is the period which immediately follows the end of the process of preparation of the fermented food product and its packaging. During this preservation period the fermented food product is usually preserved at a temperature comprised between approximately 4 and approximately 10° C.

The abovementioned fermented food product contains more than $5.10^7$, in particular more than $10^8$ *bifidobacteria* per gram of fermented food product in particular for a preservation period of at least 40 days. More particularly the above-mentioned fermented food product contains more than $5.10^7$, in particular more than $10^8$ *bifidobacteria* per gram of fermented food product up to the use-by date of the product.

The use-by dates depend on the legal preservation periods fixed by current legislation, which can typically vary from 15 to 50 days from the date of production. By way of example, the legal preservation period is generally 30 days for fresh dairy products.

A population of *bifidobacteria* which is greater than or equal to $10^8$ CFU/g at the use-by date of product preserved between 4 and 10° C. can be considered a sufficient population of *bifidobacteria* given the medical recommendations relating to the provision of *bifidobacteria* in food.

By "does not contain more than 0.5% of yeast extract or yeast autolysate", is meant in particular that the abovementioned fermented food product does not contain more than 0.5% of yeast extract or yeast autolysate at the end of its preparation process and/or that the abovementioned fermented food product does not contain more than 0.5% of yeast extract or yeast autolysate for the preservation period of at least 30 days, in particular at least 35 days, in particular at least 40 days or up to the use-by date of the abovementioned fermented food product. Moreover, the abovementioned fermented food product no longer contains a quantity greater than 0.5% of yeast extract or yeast autolysate during the process for the preparation of the product, and in particular at the time of the inoculation of the bacteria and throughout the fermentation.

By "yeast extract" and "yeast autolysate" is meant concentrates of soluble compounds of yeast cells. In this regard reference may be made in particular to the article "Yeast extracts: production, properties and components" by Rolf Sommer 9$^{th}$ International Symposium on Yeasts), from which the information below is extracted.

Yeast extracts are mainly produced by autolysis, i.e., cell hydrolysis is carried out without the addition of other enzymes. The yeast extract or yeast autolysate are used mainly in the fermentation industry and in the agri-food industry. The main raw material used in order to produce the yeast extract is constituted by yeasts with a high concentration of proteins (strains of *Saccharomyces cerevisiae*) cultured on media based on molasses or is constituted by yeasts from debittered beer (strains of *Saccharomyces cerevisiae* or *Saccharomyces uvarum*). Other raw materials used are yeasts such as *Kluyveromyces fragilis* (fermented on lactoserum) or *Candida utilis* (cultured on carbohydrate-rich waste originating from of the timber industry or on ethanol) or also special strains of baker's yeasts, in order to produce yeast extract containing 5'-nucleotides.

Autolysis is the dissociation process most frequently used in the production of yeast extract. During this process, the yeasts are degraded by their own endogenous enzymes. The autolysis process can be initiated by an osmotic shock or controlled temperature, causing cell death without inactivating the endogenous enzymes (in particular the proteases). A controlled pH, the temperature and the duration of the autolysis are decisive factors in a standardized autolysis process. By adding salts or enzymes (for example proteases or mixtures of proteases and peptidases) relative to the "standard" autolysis, the protein degradation of the yeast cells can be controlled.

Besides autolysis, the yeast extract can be produced by thermolysis (for example by boiling the yeasts in water at 100° C.), plasmolysis (treatment with strong saline solutions at a temperature below 100° C.) and mechanical degradation (high-pressure homogenization or grinding).

Then the soluble compounds are separated from the insoluble cell walls and concentrated with an evaporator with stirring or falling film evaporator, followed by optional stages of filtration, concentration under partial vacuum and rapid sterilization, Three types of yeast extract exist: liquid yeast extract (dried matter: 50 to 65%); viscous paste-type yeast extract (dried matter: 70 to 80%); dry yeast extract powder.

Taking the example of a standard yeast extract powder used in the fermentation industry, the composition is the following:
Protein content: 73-75%
Sodium: less than 0.5%
Polysaccharides: less than 5%
Oligosaccharides: less than 1%
Lipids: less than 0.5%
The protein content is typically distributed as follows:
Free amino acids: 35-40%
Di, tri and tetrapeptides (MW<600 Da): 10-15%
Oligopeptides (MW of 2000-3000 Da): 40-45%
Oligopeptides (MW of 3000-100000 Da): 2-5%
The typical cysteine content is 0.45%, and the typical methionine content is 1.12% (1.08% in the free form).

The invention relates to the use of at least one sulphur-containing amino acid, at a total concentration of approximately 5 to approximately 30 mg/l, in particular approximately 10 to approximately 15 mg/l, in particular approximately 12 to approximately 15 mg/l, and in particular 12.5 mg/l, in the free form, for the implementation of a process for the preparation of a fermented food product using ferments containing *bifidobacteria*, which fermented food product has acceptable organoleptic properties, contains more than approximately $5.10^7$, in particular more than approximately $10^8$ *bifidobacteria* per gram of fermented food product for a preservation period of at least 30 days, in particular at least 35 days and does not contain more than 0.5% yeast extract or yeast autolysate.

Moreover, the invention also relates to a fermented food product, having acceptable organoleptic properties, containing ferments comprising more than approximately $5.10^7$, in particular more than approximately $10^8$ *bifidobacteria* per gram of fermented food product for a preservation period of at least 30 days, in particular at least 35 days and having a total concentration of sulphur-containing amino acids in the free form of approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l.

More particularly, said fermented food product contains ferments comprising more than approximately $5.10^7$, in particular more than approximately $10^8$ *bifidobacteria* per gram of fermented food product for a preservation period of at least 40 days or up to the use-by date of the fermented food product.

Advantageously, the fermented food product as defined above is such that the ratio of the number of *bifidobacteria* contained in the fermented food product at the end of the preservation period to the number of *bifidobacteria* contained in the fermented food product at the start of the preservation period of at least 30 days, in particular at least 35 days, is approximately 0.2 to approximately 0.8, in particular approximately 0.3 to approximately 0.7, in particular approximately 0.4 to approximately 0.5.

In other words the survival rate of the *bifidobacteria* contained in the fermented food product between the start of the preservation period (i.e. the end of the preparation process) and the end of the preservation period is comprised between 20 and 80%, in particular between 30 and 70%, and in particular between 40 and 50%.

Said preservation period is at least 30 days, in particular at least 35 days, but more particularly at least 40 days or extends at least up to the use-by date of the fermented food product.

The invention also relates to a fermented food product preserved for a preservation period of at least 30 days, in particular at least 35 days, at a temperature of approximately 4 to approximately 10° C., having acceptable organoleptic properties and containing ferments comprising more than approximately $5.10^7$, in particular more than approximately $10^8$ bifidobacteria per gram of fermented food product.

More particularly the invention relates to a fermented food product preserved for a preservation period of at least 30 days, in particular at least 35 days, in particular at least 40 days, at a temperature of less than 12° C. or less than 10° C., having acceptable organoleptic properties and containing ferments comprising more than approximately $5.10^6$, in particular more than approximately $10^8$ bifidobacteria per gram of fermented food product.

Preferably, the invention relates to a fermented food product as defined above containing approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l, of sulphur-containing amino acids and in particular approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l of cysteine and/or approximately 5 to approximately 30 mg/l, in particular approximately 5 to approximately 15 mg/l, of methionine.

In order to determine the cysteine, it is possible to use an amino acid analyzer such as the L-8800 High Speed Amino Acid Analyzer (Hitachi High Technologies). This analyzer combines ion-exchange chromatography with colorimetric detection at two wavelengths (570 and 440 nm) after reaction with ninhydrin. It is also possible to use gas chromatography coupled with mass spectrometry or high-performance liquid chromatography coupled with fluorimetric detection.

The more particular use of cysteine is advantageous as it gives rise experimentally to a better bifidogenic effect than methionine.

The more particular use of methionine is advantageous as its cost is lower than that of the use of the cysteine.

Advantageously, said fermented food product contains less than approximately 0.5% (w/w) of substances containing more than approximately 1.7% of sulphur-containing free amino acids.

More particularly said fermented food product contains less than approximately 0.5% (w/w) of yeast extract and/or yeast autolysate and/or milk, plant or soya protein hydrolysate.

The possible presence of yeast extract or yeast autolysate type substances is easily detectable in the product by known methods. In particular, the glucans or the mannans provided by these substances are detectable. For example, the glucans and mannans being fibres, it is possible to use the total dietary fibre determination method, recommended by the AFSSA [French Agency for Food Safety] (method AOAC 985.29). The addition of yeast extract or a similar substance must also result in a complete modification of the content of all of the 20 amino acids in the product, as well as in a modification of the concentration of vitamins and minerals, relative to the normal composition of the product (for the example of milk, reference may in particular be made to the Handbook of milk composition, 1995, Academic Press).

According to a preferred embodiment, the *bifidobacteria* contained in the fermented food product as defined above are of the type *Bifidobacterium animalis*, in particular *Bifidobacterium animalis animalis* and/or *Bidifobacterium animalis lactis*, and/or *Bifidobacterium breve* and/or *Bifidobacterium longum* and/or *Bifidobacterium infantis* and/or *Bifidobacterium*

Advantageously, the fermented food product as defined above is based on plant juice and in particular fruit juice or vegetable juice such as soya juice, or on a dairy product, and in particular on cow's milk and/or on goat's milk.

Said fermented food product can also be based on sheep's milk, camel's milk or mare's milk.

By plant juice is meant a juice produced from plant extracts, in particular soya, tonyu, oat, wheat, maize etc.

Examples of vegetable juice are: tomato juice, beet juice, carrot juice etc.

Examples of fruit juice are: apple, orange, strawberry, peach, apricot, plum, raspberry, blackberry, gooseberry, pineapple, lemon, citrus fruit, grapefruit, banana, kiwi fruit, pear, cherry, passion fruit, mango, exotic fruit juice, multifruit juice etc.

According to a preferred embodiment, the ferments of the fermented food product as defined above contain lactic bacteria, in particular one or more bacteria of the genus *Lactobacillus* spp. and in particular *Lactobacillus delbrueckii bulgaricus* and/or *Lactobacillus casei* and/or *Lactobacillus reuteri* and/or *Lactobacillus acidophilus* and/or *Lactobacillus helveticus* and/or *Lactobacillus plantarum*, and/or bacteria of the type *Lactococcus cremoris* and/or *Streptococcus thermophiles* and/or *Lactococcus lactis* and/or one or more bacteria of the genus *Leuconostoc*.

Advantageously, the fermented food product as defined above is such that the proportion of *bifidobacteria* in the ferments is approximately 20 to approximately 80%, in particular approximately 30 to approximately 70%, in particular approximately 40 to approximately 60%, and in particular approximately 50%.

By "proportion of *bifidobacteria* in the ferments" is meant the proportion of *bifidobacteria* relative to the total number of bacteria included in the fermented food product, i.e. relative to all of the *bifidobacteria* and other bacteria, in particular the bacteria *Lactococcus*, *Lactobacillus*, *Streptococcus* etc.

The good numerical balance between the *bifidobacteria* and the other bacterial strains in the fermented food product at the end of the preparation process, and the substantial maintenance of this balance throughout the preservation period, are essential guarantees of the quality of the food product.

A proportion of 50% *bifidobacteria* constitutes a good compromise between the problem of cost (the *bifidobacteria* are expensive) and the problem of obtaining a correct population of *bifidobacteria*.

According to a preferred embodiment, the fermented food product as defined above is presented in the form of a stirred fermented food product or a fermented food product for drinking or a firm fermented food product or an infant fermented food product.

By "stirred [ . . . ] product" is meant a product, in particular a milk, seeded, fermented, mechanically stirred then packaged. The fermentation of such a product is carried out not in a pot but in bulk, in tanks. The curd is stirred then cooled down before being packed in pots, which are stored under refrigeration. By curd is meant a coagulate of proteins in particular of milk.

By "[ . . . ] product for drinking" is meant a product in substantially liquid form. A product for drinking is a product which is such that, after the mechanical stirring stage, the product is beaten in the tanks before being packaged.

By "firm [ . . . ] product" is meant a product (in particular a milk) seeded and directly packaged in pots where it ferments. After the seeding, the product is packaged in pots. These pots are generally placed in an oven for 3 hours. The bacteria reproduce and consume the lactose which is then partially converted to lactic acid which modifies the structure of the proteins, forming what is known as a "lactic gel". Then, the products are placed in a ventilated cooler or cooling tunnel and stored at approximately 2-4° C.

By "infant [ . . . ] product" is meant a product suited to an infant's needs, with a low protein and fat content.

Said fermented food product can in particular be a yogurt or a firm, stirred or drinking yogurt or a bar containing a dairy substance, kefir, a biscuit with a dairy filling, a water containing probiotics etc Moreover the invention also relates to a process for the preparation of a fermented food product from a starting substance, comprising
- a stage of seeding a starting substance, optionally pasteurized, by inoculation with seeding ferments containing *bifidobacteria*, in order to obtain a seeded substance,
- a stage of fermentation of the seeded substance obtained in the preceding stage in order to obtain a fermented substance,
- a stage of incorporation of at least one sulphur-containing amino acid in the free form at a concentration of approximately 5 to approximately 75 mg/l in particular approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l, this stage of incorporation being able to occur
  - either before the seeding stage,
  - or substantially simultaneously with the seeding stage,
  - or after the seeding stage and before the fermentation stage,
providing that the fermented food product does not contain more than 0.5% (w/w) of yeast extract and/or yeast autolysate.

By "fermentation" is meant a biochemical reaction which involves releasing energy from an organic substrate, under the action of micro-organisms. It is a conversion process of a raw material by the micro-organisms, this conversion then producing biomass and metabolites. In particular, lactic fermentation is an anaerobic process of the consumption of lactose by the bacteria in the ferments, which causes the formation of lactic acid and a lowering of the pH.

The invention follows from the surprising finding made by the inventors that the incorporation of sulphur-containing amino acids within the abovementioned ranges, in the absence of yeast extract and/or yeast autolysate or in the presence of a low concentration of the latter, makes it possible to improve the resistance of the *bifidobacteria* and their ability to survive. The *bidifobacteria* contained in the fermented food product at the end of the preparation process of the invention are in a better physiological state than if the stage of incorporation of sulphur-containing amino acids were omitted, which allows a larger number of these *bifidobacteria* to survive during the preservation of the fermented food product which follows.

Cysteine and/or methionine therefore have a specific bifidogenic effect. On the other hand the use of yeast extract and/or yeast autolysate, in particular at concentrations greater than 0.5% (w/w), has a tendency to stimulate all of the bacteria contained in the fermented food product, which can lead to an imbalance in the bacterial symbiosis to the detriment of the *bifidobacteria*, and in favour in particular, if they are present, of the lactic bacteria. The consequences of this imbalance are a modification of the pH, a production of acetic acid and/or of $H_2O_2$, all events which are detrimental to the quality of the product.

Moreover it should be noted that from a concentration of sulphur-containing amino acids greater than 30 mg/l, in particular from a concentration of sulphur-containing amino acids greater than 50 mg/l, and more particularly from a concentration of sulphur-containing amino acids greater than 75 mg/l, a clear degradation of the organoleptic properties of the food products is noted. This degradation is noted by means of a standard taste test as described above, which reveals the existence of a sulphur taste capable of making the products unsuitable for consumption and marketing. It should be noted that the disagreeable sulphur taste occurs in particular in the case of incorporation of cysteine and/or of methionine at more than 75 mg/l, or even in certain cases at more than 50 or 30 mg/l, but also when the concentrations of sulphur-containing amino acids exceed such values due to the presence of additional substances, for example yeast extract or yeast autolysate, in particular at a level of more than 0.5% (w/w).

Another important characteristic of the process of the invention is that the incorporation of the ferments containing the *bifidobacteria* is done directly into the starting substance intended to become the fermented food product, without necessarily resorting to artificial/synthetic intermediate growth media.

According to a particular embodiment, the process as defined above does not comprise a stage of addition of additional substances containing one or more sulphur-containing amino acids.

According to another particular embodiment, the process as defined above comprises a stage of addition of additional substances containing one or more sulphur-containing amino acids in the free form, the concentration of sulphur-containing amino acids in the free form in the additional substances being less than approximately 1.7%, preferably less than approximately 0.5%, and the concentration of said additional substances in the fermented food product being less than approximately 0.5%.

More particularly, said stage of addition of additional substances can involve addition of a yeast extract and/or yeast autolysate and/or milk, plant or soya protein hydrolysate at a concentration of less than approximately 0.5% (w/w).

Preferably, this stage of addition of additional substances takes place before the fermentation stage, for example substantially simultaneously with the seeding stage and/or simultaneously with the stage of incorporation of at least one sulphur-containing amino acid.

The benefit of an addition substantially simultaneously with the seeding stage and/or simultaneously with the stage of incorporation of at least one sulphur-containing amino acid is of a practical nature. In this case, the additional yeast extract type substances are at least partially degraded during fermentation, as they serve to supply nutrients to the ferments. Thus the concentration of the additional yeast extract type substances varies during the fermentation.

Advantageously, the process for the preparation of a fermented food product as defined above also comprises a pasteurization stage taking place before the seeding stage, making it possible to obtain a pasteurized starting substance from the starting substance.

By "pasteurization" is meant the method usual in the field of food preservation involving a rapid heating without boiling, followed by rapid cooling, making it possible to destroy most of the bacteria while partially preserving the proteins.

According to a particular embodiment, the stage of incorporation of at least one sulphur-containing amino acid takes place before the pasteurization stage, the sulphur-containing amino acid or acids being incorporated at a concentration of approximately 5 to approximately 75 mg/l, in particular approximately 5 to approximately 30 mg/l, in particular approximately 10 to approximately 15 mg/l, in particular approximately 12 to approximately 15 mg/l, and in particular 12.5 mg/l.

The benefit of incorporation before the pasteurization stage is of a practical nature.

According to another particular embodiment, the stage of incorporation of at least one sulphur-containing amino acid takes place substantially simultaneously with the seeding stage, the sulphur-containing amino acid or acids being incorporated at a concentration of approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l.

The benefit of incorporation substantially simultaneously with the seeding stage is of an economic nature (the sulphur-containing amino acid or acids are not partially destroyed by any heat treatment or pasteurization before the seeding) and of a practical nature.

According to another particular embodiment, the stage of incorporation of at least one sulphur-containing amino acid takes place after the seeding stage and before the fermentation stage, the sulphur-containing amino acid or acids being incorporated at a concentration of approximately 5 to approximately 50 mg/l, in particular approximately 5 to approximately 30 mg/l, in particular approximately 5 to approximately 20 mg/l, in particular approximately 10 to approximately 15 mg/l, in particular approximately 12 to approximately 15 mg/l, and in particular 12.5 mg/l.

The benefit of incorporation after the seeding stage and before the fermentation stage is of a practical nature and ensures an increased survival of the *bifidobacteria* during the storage of the product.

It should be noted that in the case where the incorporation of the sulphur-containing amino acid or acids takes place before the pasteurization stage, the quantity of sulphur-containing amino acids to be incorporated must be increased by approximately 30 to 50% with respect to the case where this incorporation takes place after the optional pasteurization stage, i.e. in particular substantially simultaneously with the seeding stage or after the seeding stage. In fact, in the first case some of the sulphur-containing amino acids are destroyed during the pasteurization.

In other words, the top part of the concentration range for sulphur-containing amino acids of 50-75 mg/l which is included within the concentration range for sulphur-containing amino acids provided in the invention relates more specifically to the case where the incorporation of the sulphur-containing amino acids takes place prior to a pasteurization stage.

It should be noted that it is possible to envisage dividing the stage of incorporation of sulphur-containing amino acids into two or more sub-stages, which can optionally occur at different times in the process according to the invention. The concentration of sulphur-containing amino acids which is indicated above then corresponds to the total concentration of sulphur-containing amino acids at the end of the different sub-stages of incorporation of sulphur-containing amino acids.

According to a preferred embodiment, the process for the preparation of a fermented food product as defined above comprises a stage of addition of an intermediate preparation simultaneously with the seeding stage or between the seeding stage and the fermentation stage, so as to obtain, from the seeded substance, a completed seeded substance, or after the fermentation stage, so as to obtain, from the fermented substance, a completed fermented substance, said intermediate preparation comprising a preparation of fruits and/or cereals and/or additives such as flavourings and colourings, and said stage of addition of an intermediate preparation can take place simultaneously with the stage of incorporation of at least one sulphur-containing amino acid.

The intermediate preparation can in particular contain thickeners (soluble and insoluble fibres, alginates, carragheenans, xanthan gum, pectin, starch, in particular gelatinized, gelan gum, cellulose and its derivatives, guar and carob gum, inulin) or sweeteners (aspartame, acesulphame K, saccharine, sucralose, cyclamate) or preservatives.

Examples of flavourings are: apple, orange, strawberry, kiwi fruit, cocoa flavouring etc.

Examples of colourings are: beta-carotene, carmine, cochineal red.

Moreover, the preparation of the abovementioned fruits can comprise fruits which are whole or in pieces or in jelly or in jam, making it possible for example to obtain fruit yogurts.

The intermediate preparation can also contain plant extracts (soya, rice etc.).

According to another embodiment of the invention, the seeding stage comprises inoculation with seeding ferments containing approximately $10^6$ to approximately $2.10^8$, more particularly approximately $10^6$ to approximately $10^7$ *bifidobacteria*, per ml (or per gram) of starting substance.

If a quantity of *bifidobacteria* greater than this range is inoculated, undesired acetic acid type tastes can develop. If a quantity of *bifidobacteria* less than this range is inoculated, the final quantity of *bifidobacteria* is insufficient.

Advantageously, in the process for the preparation of a fermented food product according to the invention, the *bifidobacteria* are chosen from bacteria of the type *Bifidobacterium animalis*, in particular *Bifidobacterium animalis animalis* and/or *Bidifobacterium animalis lactis*, and/or *Bifidobacterium breve* and/or *Bifidobacterium longum* and/or *Bifidobacterium infantis* and/or *Bifidobacterium bifidum*.

Particularly preferably, in the process for the preparation of a fermented food product according to the invention, the *bifidobacteria* are chosen from bacteria of the type *Bifidobacterium animalis*.

Advantageously, in the process for the preparation of a fermented food product according to the invention, the seeding ferments contain lactic bacteria, in particular one or more bacteria of the genus *Lactobacillus* spp. and in particular *Lactobacillus delbrueckii bulgaricus* and/or *Lactobacillus casei* and/or *Lactobacillus reuteri* and/or *Lactobacillus acidophilus* and/or *Lactobacillus helveticus* and/or *Lactobacillus plantarum*, and/or bacteria of the type *Lacto-*

*coccus cremoris* and/or *Streptococcus thermophilus* and/or *Lactococcus lactis* and/or one or more bacteria of the genus *Leuconostoc*.

According to an advantageous embodiment of the process for the preparation of a fermented food product as defined above, the proportion of *bifidobacteria* in the seeding ferments is approximately 20 to approximately 75%, in particular approximately 30 to approximately 50%, in particular approximately 35 to approximately 40%, in particular approximately 37.5%.

By "proportion of the *bifidobacteria* in the seeding ferments", is meant the proportion of the *bifidobacteria* relative to all of the inoculated bacteria in total during the seeding stage.

This proportion corresponds to an optimum in terms of cost and final concentration of *bifidobacteria*, given that the higher the concentration of *bifidobacteria* at the start, the more competitive they are in terms of growth relative to the other strains in the ferments, and the more rapidly the optimum concentration of *bifidobacteria* is reached.

According to a preferred embodiment of the process for the preparation of a fermented food product as defined above, the starting substance is based on plant juice and in particular fruit juice or vegetable juice such as soya juice, or on a dairy product, and in particular cow's milk and/or goat's milk.

The starting substance can also comprise sheep's and/or camel's and/or mare's milk.

In the case where the fermented food product is a dairy product, the starting substance can comprise milk, milk powder, sugar, a mixture of milk and plant juice, a mixture of milk and fruit juice, a mixture of milk and starch.

Advantageously, the process for the preparation of a fermented food product according to the invention is such that the pasteurized starting substance is a pasteurized starting substance, which is held, optionally homogenized, and cooled down, obtained from a raw material, said process comprising, before the seeding stage, the following successive stages:
  a stage of standardization of fatty substances of the raw material so as to obtain a standardized substance,
  a stage of enrichment with dried matter of the standardized substance obtained in the preceding stage, so as to obtain an enriched substance,
  a stage of pre-heating of the enriched substance obtained in the preceding stage, so as to obtain a starting substance,
  a stage of pasteurization and holding of the starting substance obtained in the preceding stage, so as to obtain a pasteurized and held substance,
  an optional stage of homogenization of the pasteurized and held substance obtained in the preceding stage, so as to obtain a pasteurized, held and optionally homogenized substance,
  a stage of initial cooling of the pasteurized, held and optionally homogenized substance obtained in the preceding stage, so as to obtain a pasteurized starting substance, held, optionally homogenized, and cooled down.

By "standardization of fatty substances" is meant a stage of bringing the quantity of fats present in the starting substance to a pre-determined level.

Enrichment with dried matter involves the addition of proteins and fatty substance in order to modify the firmness of the curd.

"Holding" involves a rapid thermization of the milk and makes it possible to destroy the vegetative microbial flora, including pathogenic forms. Its typical duration is from 4 to 10 minutes, in particular from 5 to 8 minutes, and in particular approximately 6 minutes.

By "homogenization" is meant the dispersion of the fatty substances in the milk-type substance into small fat globules. The homogenization is carried out for example at a pressure of 100 to 280 bars, in particular 100 to 250 bars, in particular 100 to 200 bars, in particular approximately 200 bars. This homogenization stage is purely optional. It is in particular absent from the production process of products with 0% fatty substances.

According to a particular embodiment, the process for the preparation of a fermented food product as defined above comprises a packaging stage between the seeding stage and the fermentation stage, said packaging stage making it possible to obtain, from the seeded substance obtained in the seeding stage, a seeded and packaged substance.

This particular embodiment corresponds to the case of the firm-type fermented food products.

More particularly, the process for the preparation of a fermented food product as defined above comprises:
  a stage of seeding a starting substance, optionally pasteurized, by inoculation with seeding ferments containing approximately $10^6$ to approximately $2.10^8$ *bifidobacteria*, more particularly approximately $10^6$ to approximately $10^7$ *bifidobacteria* per ml of starting substance, in order to obtain a seeded substance,
  a stage of packaging the seeded substance obtained in the preceding stage, in order to obtain a packaged seeded substance,
  a stage of fermentation of the packaged seeded substance obtained in the preceding stage, such that the temperature at the start of fermentation is approximately 36 to approximately 43° C., in particular approximately 37 to approximately 40° C., the temperature at the end of fermentation is approximately 37 to approximately 44° C., in particular approximately 38 to approximately 41° C., and the fermentation time is approximately 6 to approximately 11 hours, in order to obtain a fermented substance,
  a stage of final cooling of the fermented substance obtained in the preceding stage, such that the temperature at the start of the final cooling is less than approximately 22° C. and the temperature at the end of the final cooling is approximately 4 to approximately 10° C., so as to obtain a fermented food product.

According to an alternative embodiment, not involving the preparation of firm-type products, the process for the preparation of a fermented food product according to the invention comprises the following successive stages after the fermentation stage:
  a stage of intermediate cooling of the fermented substance obtained in the fermentation stage, so as to obtain a pre-cooled substance,
  a stage of storage of the pre-cooled substance obtained in the preceding stage, so as to obtain a stored substance,
  a stage of final cooling of the stored substance obtained in the preceding stage, so as to obtain a fermented food product.

According to a preferred embodiment, said fermentation stage is such that the temperature at the start of fermentation is of approximately 36 to approximately 43° C. and in particular approximately 37 to approximately 40° C., the temperature at the end of fermentation is approximately 37 to approximately 44° C. and in particular approximately 38 to approximately 41° C., and the fermentation time is approximately 6 to approximately 11 hours.

Advantageously, said intermediate cooling stage is such that the intermediate cooling time is approximately 1 hour to approximately 4 hours and in particular approximately 1 hour 30 minutes to approximately 2 hours and the intermediate cooling temperature is approximately 4 to approximately 22° C.

Preferably, said storage stage is such that the storage time is less than or equal to approximately 40 hours.

Advantageously, said final cooling stage is such that the temperature at the start of final cooling is less than approximately 22° C. and the temperature at the end of final cooling is approximately 4 to approximately 10° C.

According to a preferred embodiment, the process for the preparation of a fermented food product according to the invention comprises:
- a stage of seeding a starting substance, optionally pasteurized, by inoculation with seeding ferments containing approximately $10^6$ to approximately $110^8$, more particularly approximately $10^6$ to approximately $10^7$ bifidobacteria per ml (or per gram) of starting substance in order to obtain a seeded substance,
- a stage of fermentation of the seeded substance obtained in the preceding stage, such that the temperature at the start of fermentation is approximately 36 to approximately 43° C., in particular approximately 37 to approximately 40° C., the temperature at the end of fermentation is approximately 37 to approximately 44° C., in particular approximately 38 to approximately 41° C., and the fermentation time is approximately 6 to approximately 11 hours, in order to obtain a fermented substance,
- a stage of intermediate cooling of the fermented substance obtained in the preceding stage, such that the intermediate cooling time is approximately 1 hour to approximately 4 hours, in particular approximately 1 hour 30 minutes to approximately 2 hours and the intermediate cooling temperature is approximately 4 to approximately 22° C., so as to obtain a pre-cooled substance,
- a stage of storage of the pre-cooled substance obtained in the preceding stage, such that the storage time is less than or equal to approximately 40 hours, so as to obtain a stored substance,
- a stage of final cooling of the stored substance obtained in the preceding stage, such that the temperature at the start of final cooling is less than approximately 22° C. and the temperature at the end of final cooling is approximately 4 to approximately 10° C. so as to obtain a fermented food product.

According to a particular embodiment of the process for the preparation of a fermented food product as defined above, an additional stirring stage is provided between the fermentation stage and the intermediate cooling stage, making it possible to obtain, from the fermented substance obtained in the fermentation stage, a stirred fermented substance.

By "stirring" is meant a process of mechanical stirring using a turbine or helical stirrer. It is a stage which determines the oiliness of the product in particular the dairy product. If the stirring is too violent, incorporation of air and separation of the serum can occur. If the stirring is insufficient, the product risks subsequently becoming too thick.

According to a particular embodiment, the process for the preparation of a fermented food product according to the invention comprises, after the final cooling stage, a stage of preservation of the fermented food product at a temperature comprised between approximately 4 and approximately 10° C.

The invention also relates to a fermented food product as obtained from the process as defined above.

BRIEF DESCRIPTION OF THE DRAWING FIGURES

FIG. 1 represents a comparison of the effects of cysteine and vitamin C on the acidification of milk by the ferment of Example 1. The time in minutes is shown along the x-axis, the pH along the y-axis. Curve A: control without vitamin C or cysteine; curve B: vitamin C; curve C: cysteine.

Figure 2:
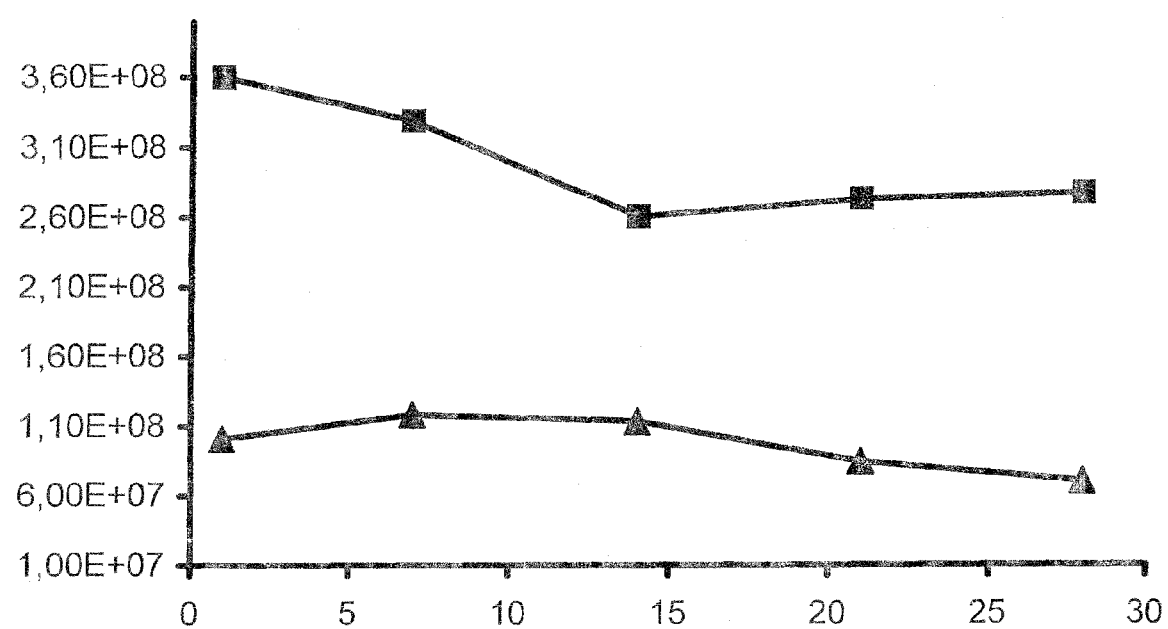

FIG. 2 represents the development of the population of bifidobacteria in the control model during preservation at 10° C. Along the x-axis, the preservation time in days; along the y-axis, the population of bifidobacteria in CFU/ml. ■: with 15 mg/l of filtered cysteine; ▲: without cysteine.

Figure 3:
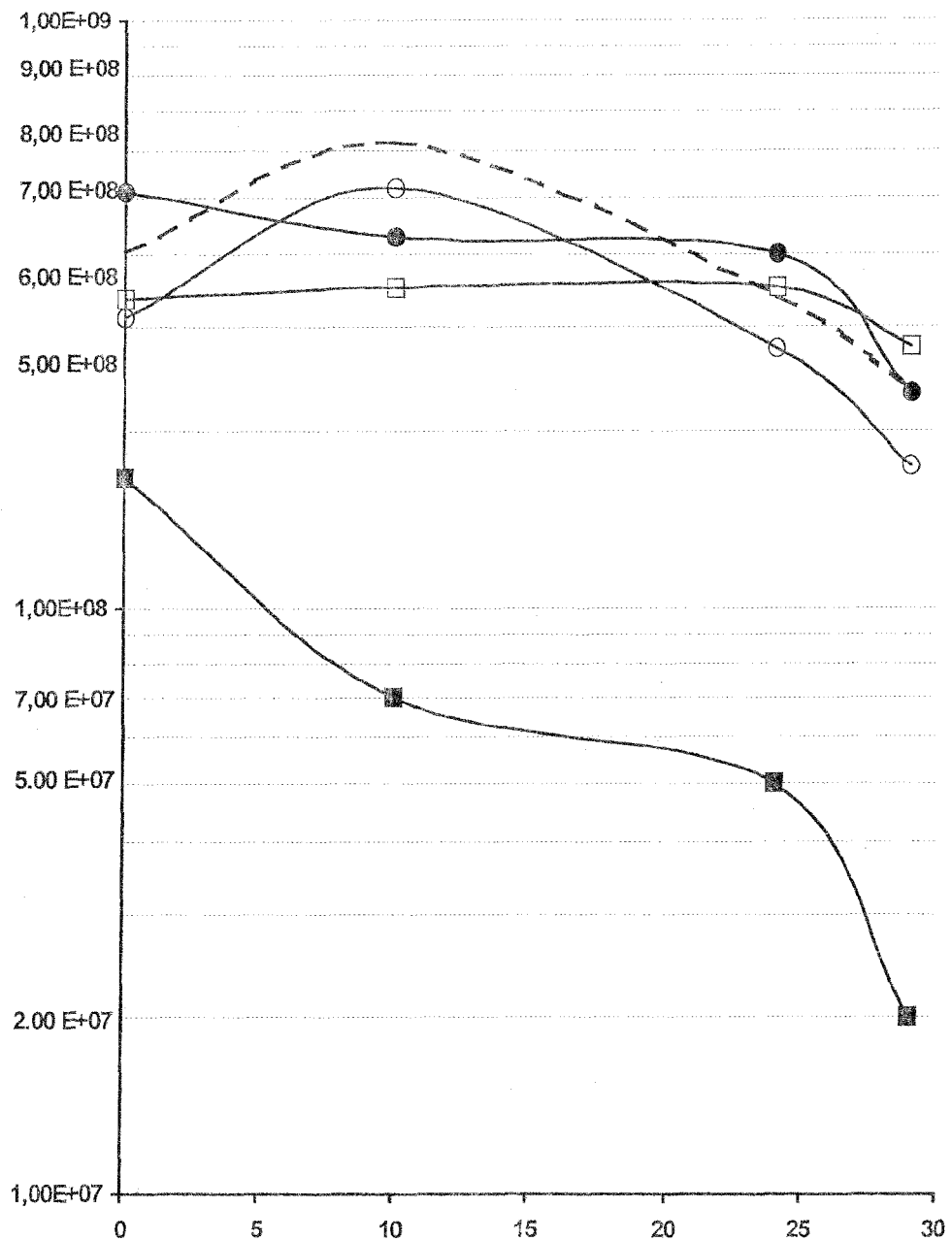

FIG. 3 represents the development of the population of bifidobacteria in the milk as a function of the treatment of the stimulant. X-axis: preservation time in days; y-axis: population in CFU/ml. Conditions: ■, control without cysteine or methionine; ○, autoclaved cysteine; ●, filtered cysteine; □, autoclaved methionine; dotted curve, filtered methionine.

Figure 4:
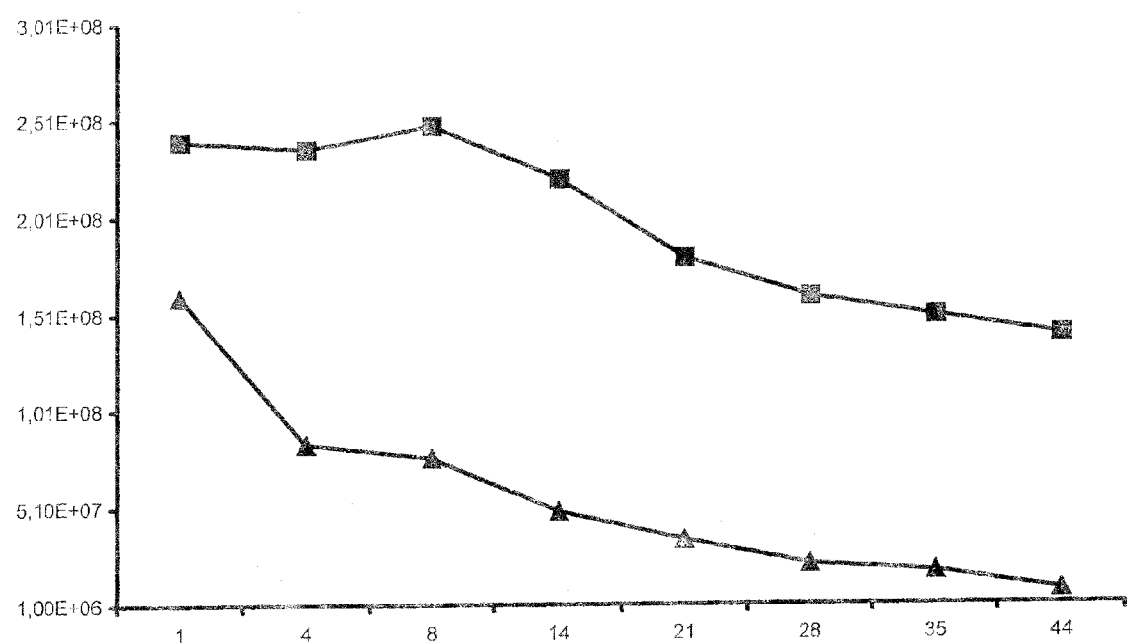

FIG. 4 represents the monitoring of the population of bifidobacteria in the control model during preservation at 10° C. X-axis: preservation time in days; y-axis: population in CFU/ml. ■: cysteine at 12 mg/l incorporated before pasteurization; ▲: control without cysteine.

DETAILED DESCRIPTION OF THE INVENTION

Examples

Example 1

Study of the Mode of Action of Cysteine as a Stimulant

A ferment comprising Streptococcus thermophilus (CNCM: I-1630)+Lactobacillus delbrueckii ssp, bulgaricus (CNCM: I-1632)+Lactobacillus delbrueckii ssp. bulgaricus (CNCM: I-1519)+Bifidobacterium animalis ssp lactic (CNCM: I-2494) is used.

This example involves studying the mode of action of cysteine as a stimulant, and determining whether it has a metabolic or antioxidant effect.

The growth of bifidobacteria in milk is measured in the presence of a solution of vitamin C (0.5 g/l) completely reducing the oxygen in the medium, and a solution of cysteine (50 mg/l).

Constitution of the Product Model:

Milex skimmed milk powder supplied by Arla food: 120 g

Water: quantity sufficient for 1 kg

A heat treatment is carried out involving pasteurization for 30 minutes at 95° C. in a bubbling water bath.

The cysteine is supplied by Sigma. The solution is prepared at 500 g/l, filtered on a 0.2 μm Naigène filter unit. This solution is used injected sterilely into the pasteurized model for a final concentration of 50 mg/l.

The vitamin C is supplied by Sigma. The solution is prepared at 100 filtered on a 0.2 μm Nalgène filter unit (cat. 156-4020, Nalge Europe Ltd, Belgium). This solution is used injected sterilely into the pasteurized model for a final concentration of 0.5 g/l.

The seeding doses of the product model are given in Table 1 which follows.

TABLE 1

Seeding doses

| | Volume for 1 l in µl | | |
|---|---|---|---|
| | Control | Filtered cysteine | Vitamin C |
| I-1630 | 100 | 100 | 100 |
| I-1519 + I-1632 | 220 | 220 | 220 |
| I-2494 | 190 | 190 | 190 |
| Cysteine | | 100 | |
| Vitamin C | | | 5 ml |

The seeding is $5.10^6$ CFU/ml of *Streptococcus thermophilus* and $5.10^6$ CFU/ml of *Lactobacillus bulgaricus*.

The monitoring of the acidification of the model at 37° C. is represented in Table 2 below as well as in FIG. 1.

TABLE 2

Monitoring of the acidification of the model

| | Vitamin C | Filtered cysteine | Control |
|---|---|---|---|
| Ta | 86 | 90 | 83 |
| Vmax | −0.0079 | −0.01046 | −0.00791 |
| pHm | 5.96 | 5.82 | 6.06 |
| Tmax | 184 | 208 | 180 |
| pH 0 | 6.5 | 6.6 | 6.7 |
| TpH 5.5 | 260 | 248 | 270 |
| TpH 5 | 391 | 354 | 412 |
| TpH 4.8 | 479 | 417 | 506 |
| D 0 CFU/ml | $1.02.10^8$ | $2.79.10^8$ | $1.47.10^8$ |

Ta = latency time (in minutes)
Vmax = maximum rate (in pH units/minute)
pHm = pH at the maximum acidification rate
Tmax = time at Vmax (in minutes)
pH 0 = pH at start of fermentation
TpH 5.5 = time to arrive at pH 5.5 (in minutes)
TpH 5 = time to arrive at pH 5 (in minutes)
TpH 4.8 = time to arrive at pH 4.8 (in minutes)
D 0 CFU/ml = quantity of bifidobacteria obtained at the end of the fermentation.

It is noted that the acidification curve in the presence of cysteine differs from the acidification curve in the presence of vitamin C, which is itself virtually indistinguishable from the control acidification curve without vitamin C or cysteine. Given that vitamin C is an antioxidant, it is deduced from this that the stimulant effect of cysteine is not an antioxidant effect but is more certainly an effect of providing essential amino acid.

Example 2

Determination of the Cysteine Stimulant Dose

A ferment comprising *Streptococcus thermophilus* (CNCM: I-2272)+*Streptococcus thermophilus* (CNCM: I-2773)+*Streptococcus thermophilus* (CNCM: I-2130)+*Lactobacillus delbrueckii* ssp. *bulgaricus* (CNCM: I-1519)+*Bifidobacterium animalis* ssp *lactis* (CNCM: I-2494) is used.

"Milk models" are constituted by standard stirred yogurts comprising the ferment described above.

The use of 0.2 µm-filtered cysteine was assessed in the "milk models" in proportions comprised from 5 mg/l to 50 mg/l (preferably from 5 to 20 mg/l).

For the *bifidobacteria* counting method, reference may be made to M. Grand et al. Quantitative analysis and molecular identification of *bifidobacteria* strains in probiotic milk products, Eur. Food Res. Technol. 217:90-92 (2003)

The population of *bifidobacteria* for the test containing the highest concentration of L cysteine is $3.10^8$ CFU/ml. at D+24 h, D corresponding to the time of packaging the product and remains stable after preservation for up to 28 days at 10° C. The standard control population (Control population D0: $1.10^8$ CFU/ml) is $9.10^7$ CFU/ml at 28 days of preservation at 10° C.

The population of *bifidobacteria* for the test containing the lowest concentration of L cysteine is $1.10^8$ CFU/ml at D+24 h.

Certain products have an undesirable taste characterized by a sulphur note which can be detected as from 0.002% of added cysteine. Below this cysteine concentration the products are accepted: a dose of 0.0015% represents a good compromise between the organoleptic constraints and constraints in terms of a *Bifidobacterium* population>$2.10^8$ CFU/ml.

Growth tests on milk carried out in the presence of 0.0015% i.e. 15 mg/l of filtered cysteine have made it possible to reach a *Bifidobacterium* I-2494 population of $2.8.10^8$ CFU/ml after 28 days of preservation at 10° C. (the development of the population relative to the control without cysteine is represented in FIG. 2).

From a sensory analysis point of view, the products produced do not have a detectable undesirable taste in comparison with the standard.

Example 3

Acidification Kinetics

The ferment described in Example 2 is used.

The acidification kinetics of milk in the presence (15 mg/L) of the optimum dose of cysteine and in the absence of cysteine (control) show the absence of the effect of the cysteine on the overall kinetics.

Example 4

Effect of the Type of Treatment of the Sulphur-Containing Amino Acid

The impact of sterilization by filtration or thermization of the cysteine and methionine is assessed (final concentration used: 50 mg/l).

The solutions are either filtered at 0.2 µm or autoclaved for 5 minutes at 121° C. then frozen in the form of beads in liquid nitrogen.

Constitution of the Model:

Miler skimmed milk powder supplied by Aria food: 120 g

Water: quantity sufficient for 1 kg

Heat treatment: pasteurization for 30 minutes at 95° C. in a bubbling water bath Cysteine: supplier Sigma. The solution is prepared at 500 g/l, filtered on a 0.2 µm Nalgène filter unit or sterilized at 121° C. for 5 minutes by an autoclave controlled by temperature probe (Fetinge France S.A., reference KL 60/101). This solution is injected sterilely into the pasteurized model for a final concentration of 50 mg/l.

Methionine: supplier Sigma. The solution is prepared at 300 g/l; the filtration or sterilization treatment is identical to that carried out for the cysteine solution. This solution is injected sterilely into the pasteurized model for a final concentration of 50 mg/l.

The seeding doses are referred to in Table 3 below.

TABLE 3

Seeding doses

| | Volume for 1 l in µl | | | | |
|---|---|---|---|---|---|
| | Control | Filtered cysteine | Autoclaved cysteine | Filtered methionine | Autoclaved methionine |
| I-1630 | 100 | 100 | 100 | 100 | 100 |
| I-1519 + I-1632 | 220 | 220 | 220 | 220 | 220 |
| I-2494 | 95 | 95 | 95 | 95 | 95 |
| Filtered cysteine | | 100 | | | |
| Autoclaved cysteine | | | 100 | | |
| Filtered methionine | | | | 100 | |
| Autoclaved methionine | | | | | 100 |

The seeding is $5.10^6$ CFU/ml of *Streptococcus thermophilus* and $5.10^6$ CFU/ml of *Lactobacillus bulgaricus*.

The monitoring of the population of *bifidobacteria* in the model preserved at 4° C. as a function of the various conditions above is represented in FIG. 3 as well as in Table 4 below:

TABLE 4

Development of the population of bifidobacteria

| | D 0 CFU/ml | D 10 CFU/ml | D 24 CFU/ml | D 29 CFU/ml |
|---|---|---|---|---|
| Filtered cysteine | $5.1.10^8$ | $4.3.10^8$ | $4.0.10^8$ | $2.3.10^8$ |
| Autoclaved cysteine | $3.1.10^8$ | $5.2.10^8$ | $2.8.10^8$ | $1.7.10^8$ |
| Filtered methionine | $4.0.10^8$ | $6.2.10^8$ | $3.4.10^8$ | $2.3.10^8$ |
| Autoclaved methionine | $3.4.10^8$ | $3.5.10^8$ | $3.5.10^8$ | $2.8.10^8$ |
| Control | $1.7.10^8$ | $7.10^7$ | $5.10^7$ | $2.10^7$ |

The reference time D0 corresponds to placing in pots (packaging). The measurements at D10, D24, D29 are carried out 10 days, 24 days, 29 days respectively after this placing in pots.

In all cases the population of *bifidobacteria* is increased by the supply of cysteine or methionine. No effect of the heat treatment on the effectiveness of the stimulants can be observed under the test conditions. The heat treatment applied to the cysteine at 50 mg/l degrades only a part thereof, the residual concentration (not assessed) is sufficient to improve the population of *bifidobacteria*.

Example 5

Development of the Population of *Bifidobacteria* During Preservation in the Case of Incorporation of Cysteine Before Pasteurization The dose of 12 mg/l of cysteine is defined as having a stimulant effect responding to the target population ($2.10^8$ CFU/ml) and responding positively in organoleptic terms (no detectable difference). This concentration was assessed on direct incorporation in the model and pasteurized composition (95° C., 30 minutes).

The monitoring of the population of *bifidobacteria* in the product model during The population of *Bifidobacterium* is $2.4.10^8$ CFU/ml at DI (i.e. 24 hours of storage) and remains stable after 44 days of preservation at 10° C. (above $1.4.10^8$ CFU/ml). The stimulant effect is clearly demonstrated relative to the standard control ($1.6.10^8$ CFU/ml at D1; $7.65.10^7$ CFU/ml at D8; $2.10^7$ CFU/ml at D28; $1.8.10^7$ CFU/ml at D35; $8.5.10^6$ CM/ml at D44) under these conditions: the population at D0 is higher when the sulphur-containing amino acids are used and the maintenance of the population during the life of the product is very much improved. This stimulant effect however remains less effective than the addition of 0.2 µm filtered cysteine to the model ($3.10^8$ CFU/ml), the heat treatment resulting in a degradation of the cysteine (residual concentration less than 15 mg/l). An initial overdosage of the quantity of cysteine is to be provided in the case where the cysteine undergoes a heat treatment.

Conclusions relating to the conditions of utilization of cysteine:
- the utilization of directly filtered cysteine (with the ferment) preserves the cysteine;
- its addition to the composition of the heat-treated model produces a slightly less good result in terms of population but account must be taken of the degradation of the cysteine during the heat treatment (less available);
- its addition via a heat-treated dairy ingredient (for example GlycoMacroPeptide corresponding to the fragment 106-169 of kappa caseine) produces less good results (less available);
- its addition in the frozen form to the ferment is possible.

Example 6

Production of a Fatty Stirred Yogurt According to the Invention on the Laboratory Scale (Micro-production)

1. Composition of the Milk and Rehydration

The stirred yogurt comprises the following ingredients: skimmed milk with 0% fat, cream with 40% fat and skimmed milk powder with 33% proteins.

Firstly, all the ingredients are combined together in order to standardize the milk at a protein level (PL) of 4.4%, a fat level of 3.5% (FL) and a dried matter level of 15.8% with stirring of the medium for 60 minutes at approximately 750 rpm with a HEIDOLPH® stirrer in order for the proteins to rehydrate.

Control of the standardization is carried out with a MILKOSCAN FT 120® infrared detector from FOSS®. Below, an example of the necessary quantities of each ingredient in order to obtain the targets characterizing the milk.

| Ingredients | In % |
|---|---|
| Skimmed milk 0% fat | 87.5 |
| Cream with 40% fat | 8.7 |
| Skimmed milk proteins 33% PL | 3.8 |
| TOTAL | 100 |

2. Homogenization

The milk is then heated between 50° C. and 60° C. in order to melt the fat globules. Once the temperature is reached, the 10 litres are homogenized with a MICROFLUIDIZER® from MICROCORPS®. This makes it possible to break up the fat globules by passing the capillary milk through a grid under a pressure of 350 bars.

3. Pasteurization

A MEMMERT® water bath is prepared and adjusted to 103° C. The milk is transferred into 8 1-litre bottles, with a precise weighing of this quantity for each bottle.

The bottles are immersed in the water bath up to the bottom of the neck at 103° C. for 35 minutes, then 10 minutes at 95° C. in the same water bath.

4. Cooling and Storage

The bottles are cooled down in a cold water bath with a continuous flow, then stored at 4° C. in a refrigerator for 12 to 24 hours according to the test schedule envisaged.

5. Holding

The milk bottles are removed from the refrigerator 45 minutes before the inoculation of the ferments and placed in a water bath at the considered fermentation temperature, i.e. 37° C.

6. Fermentation

After inoculation of the ferments ($5.10^6$ CFU/ml of *Streptococcus* thermophilus; $5.10^6$ CFU/ml of *Lactobacillus bulgaricus*; $5.10^6$ CFU/ml of *bifidobacteria*) and L-cysteine (15 mg/l) at the fermentation temperature of 37° C., the bottles are re-immersed in the water bath, and the acidification is monitored by a CINAC® from YSEBAERT® up to a pH of 4.8.

7. Cutting of Coagulum and Smoothing

The coagulum in the bottle is cut by hand. The yogurt with cut coagulum is poured into the hopper of the smoothing platform. The smoothing takes place via a metal grid with a porosity of 500 microns and the smoothed product is cooled down to 20° C. via an exchange circuit in iced water.

8. Packaging and Storage

Packaging is carried out manually in 125-ml pots and the lid is heat-sealed with a DNV-100-25 PPV-A® heat sealer from FESTO®. The products are stored in a cooler at 10° C. throughout the test.

Example 7

Assessment of the Dose of Cysteine to be Added in Order to Obtain a Product with Good Organoleptic Quality and Containing the Target Population of Bifidobacteria Different products were prepared with increasing doses of cysteine (see the table below).

The control was the standard dairy product containing the ferment.

Range:

| volume/1 L | Cysteine dose | |
|---|---|---|
| 3.2 mL | 0.0080% | 80 mg/L |
| 2 mL | 0.0050% | 50 mg/L |
| 0.8 mL | 0.0020% | 20 mg/L |
| 0.4 mL | 0.0010% | 10 mg/L |
| 0.2 mL | 0.0005% | 5 mg/L |

Each product was tasted by 4 individuals who were very familiar with the reference product from an organoleptic point of view. These individuals gave their opinions in terms of the presence of bad tastes (sulphur taste, acid note), the reference being the standard product: containing no cysteine.

Results

| Test Time | Populations (CFU/mL) | | | Sensory assessment (n = 4) |
|---|---|---|---|---|
| | T0 | T pH 4.8 | Tf 495 min | |
| 1 0.008% | 4.40E+06 | / | 1.70E+08 | Sulphur taste and/or acid note detected by all the tasters |
| 2 0.005% | 4.70E+06 | 1.90E+08 | 2.40E+08 | Sulphur taste and/or acid note detected by all the tasters |
| 3 0.002% | 3.30E+06 | 2.50E+08 | 3.10E+08 | Sulphur taste and/or acid note detected by all the tasters |
| 4 0.0015% | / | / | / | Sulphur taste and/or acid note detected by all the tasters |
| 5 0.001% | 3.10E+06 | 1.50E+08 | 2.40E+08 | No unpleasant taste detected |
| 6 0.0005% | 3.90E+06 | 1.10E+08 | 1.20E+08 | No unpleasant taste detected |

The 0.0015% dose not yet being optimum from an organoleptic point of view, the 0.00125% dose was tested. This dose represents a very good compromise between the constraint in terms of population maintenance and the constraint in terms of organoleptic quality.

The sensory profile of a product with 0.00125% (12.5 mg/l) added cysteine was produced by a jury of experts comprising 15 individuals trained in this type of tasting.

Two repetitions were carried out. The tasters had to judge the products on the basis of 23 descriptors. The results based on these descriptors (essential for defining the organoleptic quality of the product relative to the reference product) showed no significant harmful difference on the basis of these descriptors. These descriptors were the following:

Product Appearance
　Visual whey (visual assessment of the quantity of whey on the product surface)
　Texture on the spoon before stirring
　Shape holding ability (relates to the stability of the structure of the product)
　Texture on the spoon after stirring of the product
　Thickness (resistance to the movement of the spoon)
　Thread (continuity of the flow thread)
　Covering (quantity of product which covers the back of the spoon)
Texture in the Mouth after Stirring of the Product
　Melting away (speed of disappearance of the product in the mouth)
　Coating (coats the inside of the mouth)
　Soft (Tactile sensation of softness in the mouth)
Flavours
　Acid
　Sweet
　Bitter
　Astringent
　Milk Flavourings
　Unpleasant tastes
　Cream
　Butter
　Milk
　Fromage frais Acetaldehyde
Lactoserum
Lactone
Lemon
Potato The sought result is an absence of significant difference between the control product and the product supplemented with cysteine.

In the present case, a product according to the invention, supplemented with 12.5 mg/l of cysteine exhibits no significant difference in terms of appearance, texture, flavours and tastes relative to the control product.

The invention claimed is:

1. A fermented milk product, comprising ferments comprising *Lactobacillus delbrueckii bulgaricus, Streptococcus thermophilus* and *bifidobacteria*, said fermented milk product having more than $5\times10^7$ *bifidobacteria* per gram of fermented milk product lasting for a preservation period of at least 30 days, and
    a sulfur containing amino acid,
        wherein said fermented milk product has a total concentration of sulfur containing amino acids in less than 15 mg/l.

2. The fermented milk product according to claim 1, said fermented milk product comprising more than $10^8$ *bifidobacteria* per gram of fermented milk product for the preservation period of at least 30 days.

3. The fermented milk product according to claim 1, in which a ratio of a number of *bifidobacteria* contained in the fermented milk product at an end of the preservation period to a number of *bifidobacteria* contained in the fermented milk product at a start of the preservation period of at least 30 days, is 0.2 to 0.8.

4. The fermented milk product according to claim 1, comprising less than 15 mg/l, of cysteine and/or less than 15 mg/l, of methionine.

5. The fermented milk product according to claim 1, comprising less than 0.5% (w/w) of substances containing more than 1.7% sulfur-containing free amino acids.

6. The fermented milk product according to claim 1, comprising less than 0.5% (w/w) of yeast extract and/or yeast autolysate and/or milk, plant or soya protein hydrolysate.

7. The fermented milk product according to claim 1, in which the *bifidobacteria* is *Bifidobacterium animalis animalis, Bifidobacterium animalis lactis, Bifidobacterium breve, Bifidobacterium longum, Bifidobacterium infantis, Bifidobacterium bifidum* or combinations thereof.

8. The fermented milk product according to claim 1, said fermented milk product is based on cow's milk and/or goat's milk.

9. The fermented milk product according to claim 1, said ferments further comprise lactic bacteria.

10. The fermented milk product according to claim 1, in which the proportion of *bifidobacteria* in the ferments is 20 to 80%.

11. The fermented milk product according to claim 1, said fermented milk product is in the form of a stirred fermented milk product or a fermented milk product for drinking or an infant fermented milk product.

12. The fermented milk product according to claim 1, wherein the preservation period is at least 35 days.

13. The fermented milk product according to claim 1, said ferments further comprising one or more bacteria of *Lactobacillus casei, Lactobacillus reuteri, Lactobacillus helveticus, Lactobacillus plantarum, Lactococcus cremosis, Streptococcus lactic,* and *Leuconostoc* or combinations thereof.

14. The fermented milk product according to claim 1, said ferments further comprising one or more bacteria of the genus *Lactococcus* cremosis.

15. A fermented milk product, comprising ferments comprising *Lactococcus* cremosis, *Lactobacillus delbrueckii bulgaricus, Streptococcus thermophilus* and *bifidobacteria*, said fermented milk product having more than $5\times10^7$ *bifidobacteria* per gram of fermented milk product lasting for a preservation period of at least 30 days, and
    a sulfur containing amino acid,
        wherein said product has a total concentration of sulfur containing amino acids in free form of less than 15 mg/l.

16. The fermented milk product according to claim 1, which does not contain more than 0.5% yeast extract or yeast autolysate.

17. The fermented milk product according to claim 15, which does not contain more than 0.5% yeast extract or yeast autolysate.

18. A fermented milk product, comprising ferments comprising *Lactobacillus delbrueckii bidgaricus, Streptococcus thermophilus* and *bifidobacteria*, said product having more than $5\times10^7$ *bifidobacteria* per gram of fermented food product lasting for a preservation period of at least 30 days, and
    a sulfur-containing amino acid,
        wherein said fermented milk product has a total concentration of cysteine or derivatives or salts thereof in free form of less than 15 mg/l, and the fermented milk product does not contain more than 0.5% yeast extract or yeast autolysate.

* * * * *